(12) United States Patent
Kabiri Bamoradian et al.

(10) Patent No.: US 11,512,063 B2
(45) Date of Patent: Nov. 29, 2022

(54) FUNCTIONALIZED BIO-BASED CROSSLINKERS

(71) Applicants: Kourosh Kabiri Bamoradian, Tehran (IR); Zeinab Karami, Tehran (IR); Mohammad Jalaloddin Zohuriaan-Mehr, Tehran (IR)

(72) Inventors: Kourosh Kabiri Bamoradian, Tehran (IR); Zeinab Karami, Tehran (IR); Mohammad Jalaloddin Zohuriaan-Mehr, Tehran (IR)

(*) Notice: Subject to any disclaimer, the term of this patent is extended or adjusted under 35 U.S.C. 154(b) by 0 days.

(21) Appl. No.: 16/986,283

(22) Filed: Aug. 6, 2020

(65) Prior Publication Data

US 2020/0361889 A1 Nov. 19, 2020

Related U.S. Application Data

(60) Provisional application No. 62/883,123, filed on Aug. 6, 2019.

(51) Int. Cl.
*C07D 303/16* (2006.01)
*C07D 301/36* (2006.01)

(52) U.S. Cl.
CPC .......... *C07D 303/16* (2013.01); *C07D 301/36* (2013.01)

(58) Field of Classification Search
CPC .............................. C07D 303/16; C07D 301/36
See application file for complete search history.

(56) References Cited

U.S. PATENT DOCUMENTS 2,801,232 A * 7/1957 Suen ............... C08G 59/62
528/361
2,940,986 A * 6/1960 Newey ............ C07D 303/16
549/557

FOREIGN PATENT DOCUMENTS

| CN | 102863404 A * | 1/2013 | |
| CN | 107935606 A * | 4/2018 | ......... C04B 33/1305 |
| WO | WO-0130881 A1 * | 5/2001 | ............. C08G 59/12 |

OTHER PUBLICATIONS

Maiorana et al. Journal of Polymer Chemistry 2016, 54, 2625-2631 (Year: 2016).*
Beardslee et al. Lipid Technology 2012, 24, 223-225 (Year: 2012).*
Maerker et al. Journal of Applied Polymer Science 1963, 7, 301-307 (Year: 1963).*

* cited by examiner

*Primary Examiner* — Matthew P Coughlin
(74) *Attorney, Agent, or Firm* — Bajwa IP Law Firm; Haris Zaheer Bajwa

(57) ABSTRACT

A method for synthesizing functionalized bio-based crosslinkers including forming a first mixture by mixing a bio-based carboxylic acid with an alkaline solution and forming a second mixture containing a functionalized bio-based crosslinker by reacting the bio-based carboxylic acid with a modifier. The modifier includes at least one of an epoxide group and an acrylate group. Reacting the bio-based carboxylic acid with the modifier includes forming a reaction mixture by mixing the first mixture with the modifier and exposing the reaction mixture to at least one of heating, ultrasound radiation, and microwave radiation.

7 Claims, 15 Drawing Sheets

FUNCTIONALIZED BIO-BASED CROSSLINKERS

CROSS-REFERENCE TO RELATED APPLICATION

This application claims the benefit of priority from U.S. Provisional Patent Application Ser. No. 62/883,123, filed on Aug. 6, 2019, and entitled "PREPARATION OF BIO-BASED CROSSLINKERS FOR SUPERABSORBENT POLYMER APPLICATIONS," which is incorporated herein by reference in its entirety.

TECHNICAL FIELD

The present disclosure generally relates to crosslinkers, particularly to bio-based crosslinkers for fabricating superabsorbent polymers, and more particularly to a method for synthesizing functionalized bio-based crosslinkers.

BACKGROUND

Superabsorbent polymers (SAPs) are three-dimensional hydrophilic networks which absorb and retain large amounts of water and physiological solutions. Superabsorbent polymers are industrially fabricated using monomers, initiators, and crosslinkers in which type and content of the crosslinkers have a key role in determining the superabsorbent properties. However, SAPs fabricated using conventional crosslinkers may have limited applications due to their poor physicochemical and swelling characteristics.

Moreover, conventional crosslinkers are generally composed of fossil-based materials which cause environmental pollution and have limited resources. There is a lot of interest in replacing fossil-based crosslinkers with renewable materials for fabricating the SAPs. As a result, bio-based materials are suitable candidates due to their sustainability, safety, and cost-effectiveness. For example, biomass is a huge sustainable source for the production of different chemicals, such as lactic acid, itaconic acid, succinic acid, tartaric acid, and citric acid.

Hence, there is a need for a simple and efficient method for synthesizing bio-based crosslinkers. Also, there is a need for bio-based crosslinkers which may be utilized as an internal crosslinker for fabricating cost-effective SAPs with improved swelling properties and which may be used as an external crosslinker for surface treatment of SAP particles.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for synthesizing exemplary functionalized bio-based crosslinkers including forming a first mixture by mixing a bio-based carboxylic acid with an alkaline solution and forming a second mixture containing a functionalized bio-based crosslinker by reacting the bio-based carboxylic acid with a modifier. In an exemplary embodiment, reacting the bio-based carboxylic acid with the modifier may include forming a reaction mixture by mixing the first mixture with the modifier and exposing the reaction mixture to at least one of heating, ultrasound radiation, and microwave radiation.

In an exemplary embodiment, the modifier may include at least one of an epoxide group and an acrylate group. In an exemplary embodiment, mixing the first mixture with the modifier may include mixing the first mixture with at least one of glycidyl methacrylate (GMA) and epichlorohydrin (ECH). In an exemplary embodiment, mixing the first mixture with the modifier may include mixing the first mixture containing a bio-based dicarboxylic acid with the modifier.

In an exemplary embodiment, mixing the first mixture containing the bio-based dicarboxylic acid with the modifier may include mixing the first mixture containing at least one of citric acid, itaconic acid, tartaric acid, and succinic acid with the modifier. In an exemplary embodiment, mixing the first mixture with the modifier may include mixing the first mixture containing the itaconic acid with the GMA at a molar ratio of GMA/itaconic acid between about two (2) and about six (6). In an exemplary embodiment, mixing the first mixture with the modifier may include mixing the first mixture containing the succinic acid with the GMA at a molar ratio of GMA/succinic acid between about two (2) and about six (6).

In an exemplary embodiment, mixing the first mixture with the modifier may include mixing the first mixture containing the tartaric acid with the GMA at a molar ratio of GMA/tartaric acid between about two (2) and about eight (8). In an exemplary embodiment, mixing the first mixture with the modifier may include mixing the first mixture containing the citric acid with the GMA at a molar ratio of GMA/citric acid between about two (2) and about eight (8). In an exemplary embodiment, mixing the first mixture with the modifier may include mixing the first mixture containing the bio-based carboxylic acid with the ECH at a molar ratio of ECH/bio-based carboxylic acid between about two (2) and about ten (10).

In an exemplary embodiment, exposing the reaction mixture to at least one of the heating, the ultrasound radiation, and the microwave radiation. In an exemplary embodiment, exposing the reaction mixture to at least one of the heating, the ultrasound radiation, and the microwave radiation may include heating the reaction mixture to a temperature between about 30° C. and about 95° C. In an exemplary embodiment, heating the reaction mixture may include heating the second mixture for a time period between about thirty (30) minutes and about six (6) hours.

In an exemplary embodiment, mixing the bio-based carboxylic acid with the alkaline solution may include mixing the bio-based carboxylic acid with the alkaline solution at a molar ratio of alkaline material/bio-based carboxylic acid between about two (2) and about five (5). In an exemplary embodiment, mixing the bio-based carboxylic acid with the alkaline solution may include mixing the bio-based carboxylic acid with at least one of sodium hydroxide, lithium hydroxide, and potassium hydroxide.

In one general aspect, the present disclosure describes an exemplary functionalized bio-based crosslinker including a bio-based carboxylic acid, a modifier with a functional group of at least one of an epoxide group and an acrylate group, and an alkaline material. In an exemplary embodiment, the bio-based carboxylic acid may be covalently bound to the functional group of the modifier. In an exemplary embodiment, the modifier may include at least one of glycidyl methacrylate (GMA) and epichlorohydrin (ECH).

In an exemplary embodiment, the exemplary functionalized bio-based crosslinker may include the GMA and the bio-based carboxylic acid with a molar ratio between two (2) and about eight (8). In an exemplary embodiment, the exemplary functionalized bio-based crosslinker may include the bio-based carboxylic acid and the ECH with a molar ratio between two (2) and about five (5). In an exemplary embodiment, the bio-based carboxylic acid may include a bio-based dicarboxylic acid. In an exemplary embodiment, the bio-based carboxylic acid may include at least one of citric acid, itaconic acid, tartaric acid, and succinic acid. In an exemplary embodiment, the alkaline material may include at least one of sodium hydroxide, lithium hydroxide, and potassium hydroxide.

Other exemplary systems, methods, features, and advantages of the implementations will be or will become, apparent to one of ordinary skill in the art upon examination of the following figures and detailed description. It is intended that all such additional systems, methods, features, and advantages be included within this description and this summary, be within the scope of the implementations and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Disclosed herein is an exemplary method for synthesizing exemplary functionalized bio-based crosslinkers by functionalizing bio-based carboxylic acids with at least an epoxy group and an acrylate group. In an exemplary embodiment, functionalization of the bio-based carboxylic acids may improve their potency for fabricating three-dimensional networks of superabsorbent polymers (SAPs) with enhanced swelling properties. The exemplary functionalized bio-based crosslinkers may be used as internal or external crosslinkers for fabricating SAPs with higher saline absorbency and higher absorbency under load.

Figure 1A:
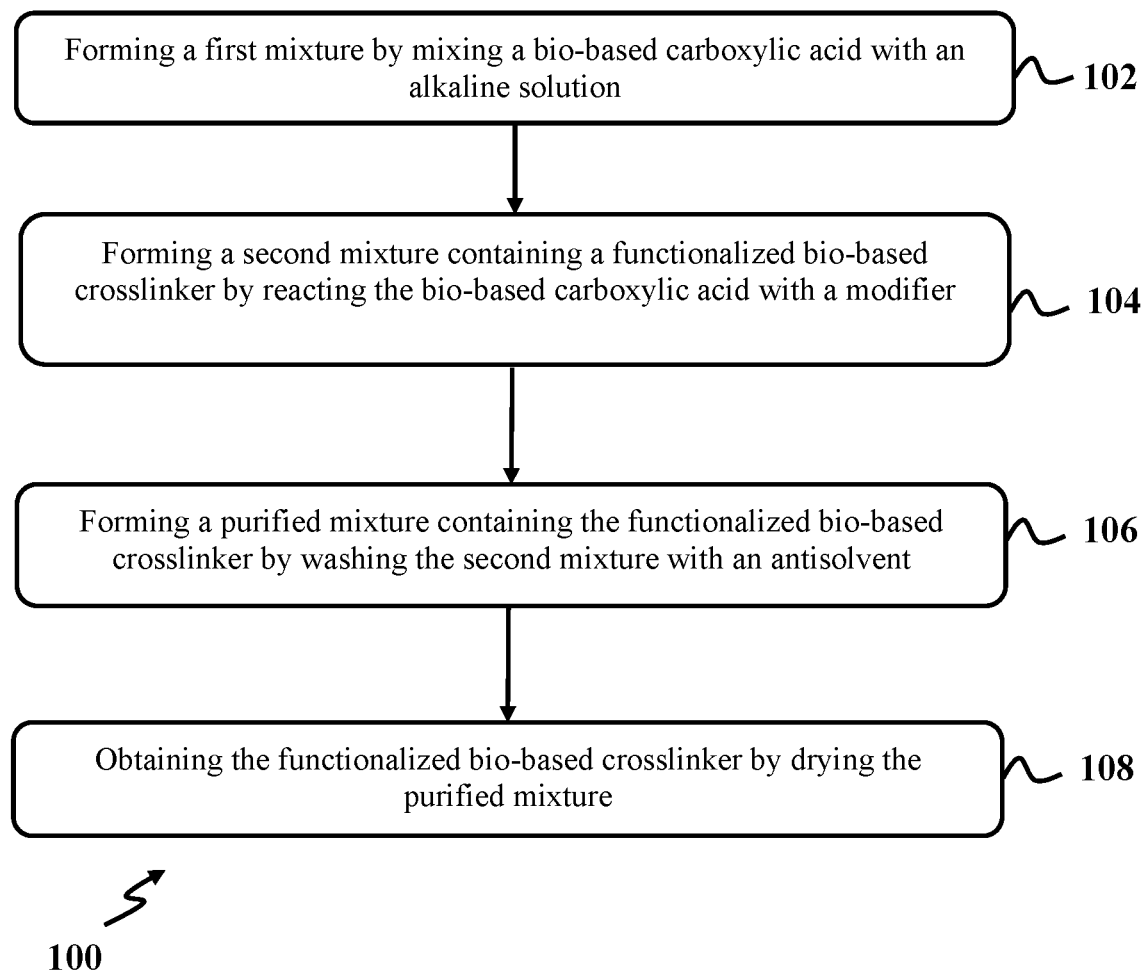
FIG. 1A shows a flowchart of an exemplary method for synthesizing functionalized bio-based crosslinkers, consistent with one or more exemplary embodiments of the present disclosure.

FIG. 1A shows a flowchart of an exemplary method 100 for synthesizing functionalized bio-based crosslinkers, consistent with one or more exemplary embodiments of the present disclosure. An exemplary method 100 may include forming a first mixture by mixing a bio-based carboxylic acid with an alkaline solution (step 102), forming a second mixture containing a functionalized bio-based crosslinker by reacting the bio-based carboxylic acid with a modifier (step 104), forming a purified mixture containing the functionalized bio-based crosslinker by washing the second mixture with an antisolvent (step 106), and obtaining the functionalized bio-based crosslinker by drying the purified mixture (step 108).

In further detail with respect to step 102, in an exemplary embodiment, the exemplary method may include forming a first mixture by mixing a bio-based carboxylic acid with an alkaline solution. In an exemplary embodiment, mixing the bio-based carboxylic acid with the alkaline solution may include mixing the bio-based carboxylic acid with the alkaline solution at a molar ratio of alkaline material/bio-based carboxylic acid between about two (2) and about five (5).

In an exemplary embodiment, mixing the bio-based carboxylic acid with the alkaline solution may include mixing at least one of citric acid, itaconic acid, tartaric acid, and succinic acid with the alkaline solution. In an exemplary embodiment, mixing the bio-based carboxylic acid with the alkaline solution may include mixing a solution of the bio-based carboxylic acid with the alkaline solution. In an exemplary embodiment, mixing the bio-based carboxylic acid with the alkaline solution may include mixing the bio-based carboxylic acid with at least one of sodium hydroxide, lithium hydroxide, and potassium hydroxide.

In further detail with respect to step 104, in an exemplary embodiment, the exemplary method may include forming a second mixture containing a functionalized bio-based crosslinker by chemically reacting the bio-based carboxylic acid with a modifier. In an exemplary embodiment, chemically reacting the bio-based carboxylic acid with a modifier may include forming chemical bonds between epoxy groups of the modifier and carboxyl groups of the bio-based carboxylic acid.

Figure 1B:
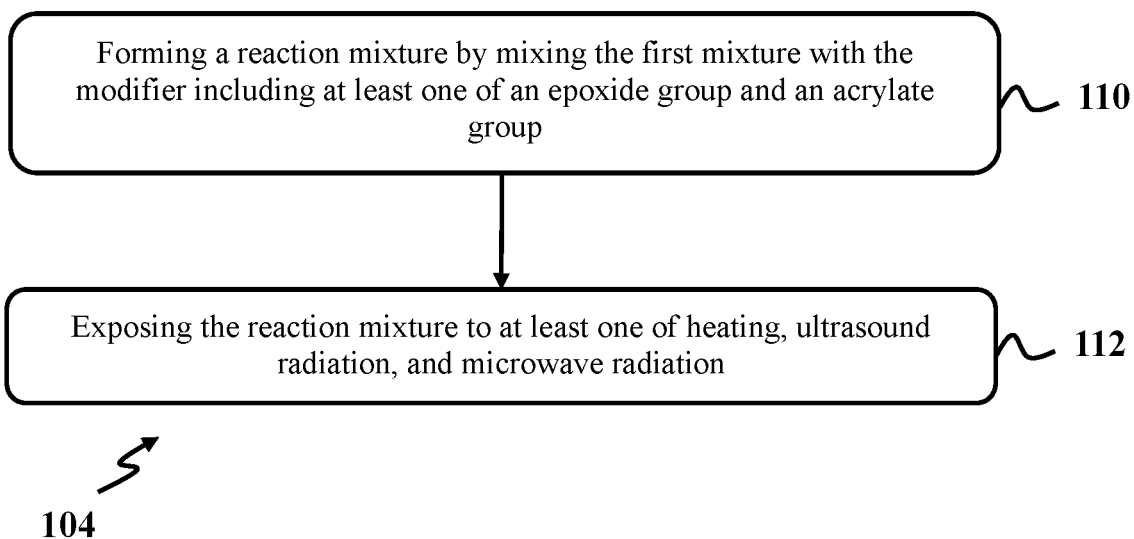
FIG. 1B shows a flowchart of an exemplary method for forming a second mixture containing a functionalized bio-based crosslinker by reacting the bio-based carboxylic acid with a modifier, consistent with one or more exemplary embodiments of the present disclosure.

Details regarding step 104 are illustrated in FIG. 1B. In detail, FIG. 1B shows a flowchart of an exemplary method for forming the second mixture containing the functionalized bio-based crosslinker by reacting the bio-based carboxylic acid with the modifier, consistent with one or more exemplary embodiments of the present disclosure. Referring to FIG. 1B, reacting the bio-based carboxylic acid with the modifier may include forming a reaction mixture by mixing the first mixture with the modifier including at least one of an epoxide group and an acrylate group (step 110) and exposing the reaction mixture to at least one of heating, ultrasound radiation, and microwave radiation (step 112).

In further detail with respect to step 110, in an exemplary embodiment, mixing the first mixture with the modifier may include mixing the first mixture with at least one of glycidyl methacrylate (GMA) and epichlorohydrin (ECH). In an exemplary embodiment, mixing the first mixture with the modifier may include mixing the first mixture containing itaconic acid with GMA at a molar ratio of GMA/itaconic acid between about two (2) and about six (6).

In an exemplary embodiment, mixing the first mixture with the modifier may include mixing the first mixture containing succinic acid with GMA at a molar ratio of GMA/succinic acid between about two (2) and about six (6). In an exemplary embodiment, mixing the first mixture with the modifier may include mixing the first mixture containing tartaric acid with GMA at a molar ratio of GMA/tartaric acid between about two (2) and about eight (8). In an exemplary embodiment, mixing the first mixture with the modifier may include mixing the first mixture containing citric acid with GMA at a molar ratio of GMA/citric acid between about two (2) and about eight (8).

In an exemplary embodiment, mixing the first mixture with the modifier may include mixing the first mixture containing the bio-based carboxylic acid with the ECH at a molar ratio of ECH/bio-based carboxylic acid between about two (2) and about ten (10). In an exemplary embodiment, mixing the first mixture containing the bio-based carboxylic acid with the ECH may include mixing the first mixture containing the bio-based carboxylic acid with a solution of the ECH. In an exemplary embodiment, the solution of the ECH may be prepared by dissolving the ECH in an organic solvent. In an exemplary embodiment, the solution of the ECH may include the organic solvent and the ECH with a molar ratio between about five (5) and about ten (10). In an exemplary embodiment, the organic solvent may include at least one of 2-propanol and butanol.

In further detail with respect to step 112, in an exemplary embodiment, exposing the reaction mixture to at least one of the heating, the ultrasound radiation, and the microwave radiation may include heating the reaction mixture to a temperature between about 30° C. and about 95° C. In an exemplary embodiment, heating the reaction mixture may include heating the second mixture for a time period between about thirty (30) minutes and about six (6) hours.

In an exemplary embodiment, chemically reacting the bio-based carboxylic acid with the modifier may include chemically reacting the bio-based carboxylic acid with the modifier at atmospheric pressure. In an exemplary embodiment, chemically reacting the bio-based carboxylic acid with the modifier may include reacting the bio-based carboxylic acid with the modifier with a molar ratio of the modifier to the bio-based carboxylic acid between about 2 and about 8.

Referring back to FIG. 1A, in further detail with respect to step 106, in an exemplary embodiment, the exemplary method may include forming a purified mixture containing the functionalized bio-based crosslinker by washing the second mixture with an antisolvent at room temperature. In an exemplary embodiment, washing the second mixture with the antisolvent may include washing the second mixture with at least one of heptane and toluene. In an exemplary embodiment, the purified mixture may be formed through a solvent extraction method. In the present disclosure, "solvent extraction method" may refer to a method for separating functionalized bio-based crosslinker based on its relative solubility in two different immiscible liquids, usually water and an organic solvent.

In further detail with respect to step 108, in an exemplary embodiment, the exemplary method may include obtaining the functionalized bio-based crosslinker by drying the purified mixture. In an exemplary embodiment, drying the purified mixture may include drying the purified mixture at a temperature between about 50° C. and about 70° C. in an air-forced oven. In an exemplary embodiment, drying the purified mixture may include drying the purified mixture for a time period between about one (1) hour and three (3) hours.

In an exemplary embodiment, the exemplary functionalized bio-based crosslinker may include a bio-based carboxylic acid, a modifier, and an alkaline material. In an exemplary embodiment, the modifier may include a functional group including at least one of the epoxide group and the acrylate group. In an exemplary embodiment, the bio-based carboxylic acid may be covalently bound to the functional group of the modifier. In an exemplary embodiment, the modifier may include at least one of GMA and ECH. In an exemplary embodiment, the bio-based carboxylic acid may include at least one of citric acid, itaconic acid, tartaric acid, and succinic acid. In an exemplary embodiment, the alkaline material may include at least one of sodium hydroxide, lithium hydroxide, and potassium hydroxide.

In an exemplary embodiment, a functionalized bio-based crosslinker may include GMA and a bio-based carboxylic acid with a molar ratio between about two (2) and about twenty-five (25). In an exemplary embodiment, the functionalized bio-based crosslinker may include ECH and a bio-based carboxylic acid with a molar ratio between about two (2) and about ten (10). In the present disclosure, "functionality" of the exemplary functionalized bio-based crosslinkers may refer to a ratio of GMA/the bio-based carboxylic acid in the formation of exemplary functionalized bio-based crosslinkers.

In an exemplary embodiment, an exemplary functionalized bio-based crosslinkers may be used as an internal crosslinker or as an external crosslinker for fabricating SAPs and hydrogels. In an exemplary embodiment, an exemplary functionalized bio-based crosslinkers may be used as an external crosslinker for surface treatment of the SAPs. In an exemplary embodiment, an exemplary functionalized bio-based crosslinkers may be used as an external crosslinker for surface treatment of an SAPs with a weight ratio of an exemplary functionalized bio-based crosslinkers to SAP particles between 50 grams and 200 grams per one (1) Kg of SAP particles. In an exemplary embodiment, an exemplary functionalized bio-based crosslinkers may be used as an internal crosslinker or used as an external crosslinker for fabricating acrylic-based SAPs.

In an exemplary embodiment, an exemplary functionalized bio-based crosslinkers may be used for fabricating acrylic-based SAPs by crosslinking acrylic acid monomers with an amount of an exemplary functionalized bio-based crosslinkers between about 2.5 grams and about ten (10) grams per one (1) Kg of the acrylic acid monomers. In an exemplary embodiment, increasing the functionality of an exemplary functionalized bio-based crosslinkers may aid in reducing the required amount of the internal and external crosslinkers needed for fabricating the SAPs due to more crosslinking of the acrylic acid monomers.

In an exemplary embodiment, exemplary SAPs fabricated using the exemplary functionalized bio-based crosslinkers may have improved swelling properties, such as higher water and saline absorbency and higher absorbency under load (AUL) value than conventional SAPs. In an exemplary embodiment, exemplary SAPs fabricated using functionalized bio-based crosslinkers may have a swelling capacity in water up to about 1104 g/g. In an exemplary embodiment, exemplary SAPs fabricated using functionalized bio-based crosslinkers may have saline absorbency of up to about 119 g/g. In an exemplary embodiment, exemplary SAPs fabricated using functionalized bio-based crosslinkers may have AUL up to 22 g/g. In an exemplary embodiment, the exemplary surface-treated SAPs using the functionalized bio-based crosslinkers may have AUL up to 30 g/g.

EXAMPLES

Example 1: Synthesis of Functionalized Citric Acid-Based Crosslinkers

In this example, functionalized citric acid (CA)-based crosslinkers were synthesized using GMA and ECH utilizing a process similar to exemplary method 100 as presented in FIG. 1. In order to functionalize the citric acid with GMA, a first mixture was formed by mixing a sodium hydroxide (NaOH) solution with a citric acid solution at a molar ratio of about 3. The citric acid solution was prepared by dissolving about two (2) grams of citric acid in fifteen (15) ml of water. Mixing the citric acid solution with the NaOH solution was done in a two-necked flask equipped with a magnetic stirrer.

After that, the second mixture was formed by adding GMA to the first mixture under a stirring condition at a temperature of about 70° C. and for two different time periods of about two (2) hours and about four (4) hours. The molar ratio of GMA/citric acid was between about two (2) and about three (3). TABLE. 1 represents four functionalized citric acid-based crosslinker synthesized in various conditions. In the next step, the second mixture was washed using heptane while stirring and an aqueous phase containing functionalized citric acid was separated. In the end, the citric acid functionalized using GMA (CA-GMA) was obtained by drying the aqueous phase at a temperature of about 50° C. in an oven.

TABLE 1

Different conditions for the synthesis of functionalized citric acid-based crosslinkers

| Name | Citric acid (g) | GMA (g) | NaOH (g) | Temperature (° C.) | Time (h) |
| --- | --- | --- | --- | --- | --- |
| CA-GMA-1 | 2 | 4.43 | 1.2 | 70 | 2 |
| CA-GMA-2 | 2 | 2.95 | 1.2 | 70 | 2 |
| CA-GMA-3 | 2 | 2.95 | 1.2 | 70 | 2 |
| CA-GMA-4 | 2 | 2.95 | 1.2 | 70 | 4 |

Also, in order to functionalize citric acid using the ECH, a first mixture was formed by mixing a NaOH solution with a CA solution at a molar ratio of about 2. The citric acid solution was prepared by dissolving about two (2) grams of citric acid in fifteen (15) ml of water. After that, a second mixture was formed by mixing the first mixture with a solution of ECH with a concentration of about 1.5 M in a two-necked flask equipped with a magnetic stirrer. The second mixture contained CA and ECH with a molar ratio of ECH/CA of about two (2).

The second mixture was stirred at a temperature of about 90° C. for a time period of about three (3) hours. In the next step, the second mixture was washed using heptane while stirring and, as a result, an aqueous phase containing functionalized citric acid was separated from the second mixture. In the end, the citric acid functionalized using ECH (CA-ECH) was obtained by drying the aqueous phase at a temperature of about 50° C. in an oven.

Figure 2A:
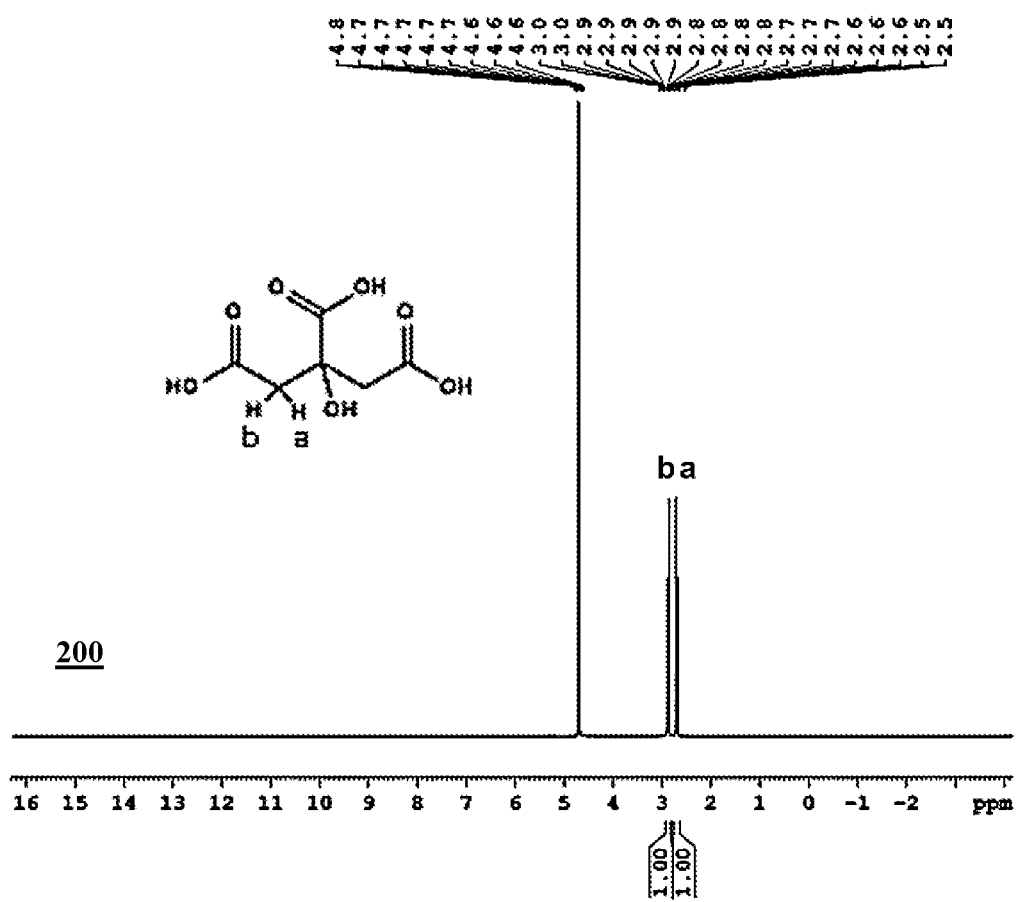
FIG. 2A illustrates a proton nuclear magnetic resonance ($^1$H NMR) spectrum of citric acid (CA), consistent with one or more exemplary embodiments of the present disclosure.
Figure 2B:
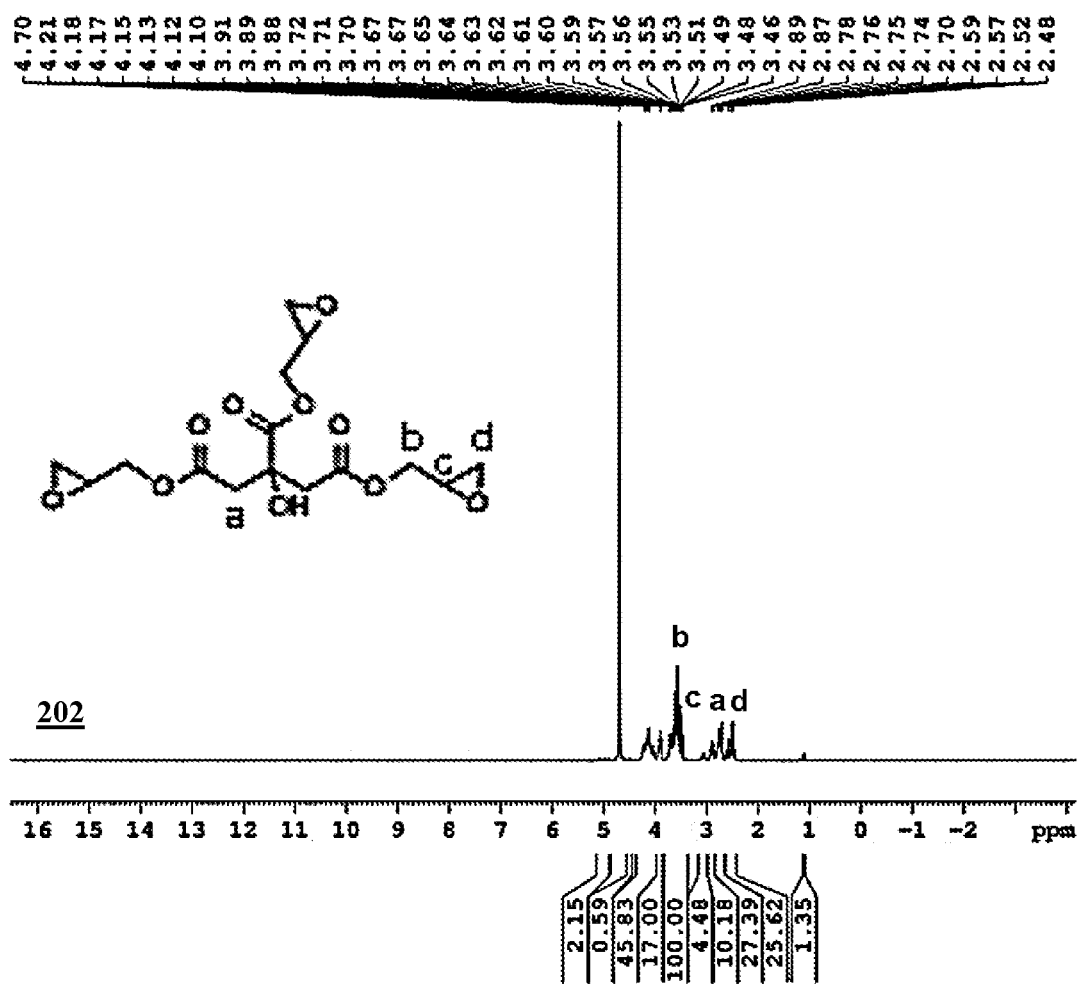
FIG. 2B illustrates a $^1$H NMR spectrum of a citric acid-based crosslinker functionalized using epichlorohydrin (CA-ECH), consistent with one or more exemplary embodiments of the present disclosure.
Figure 2C:
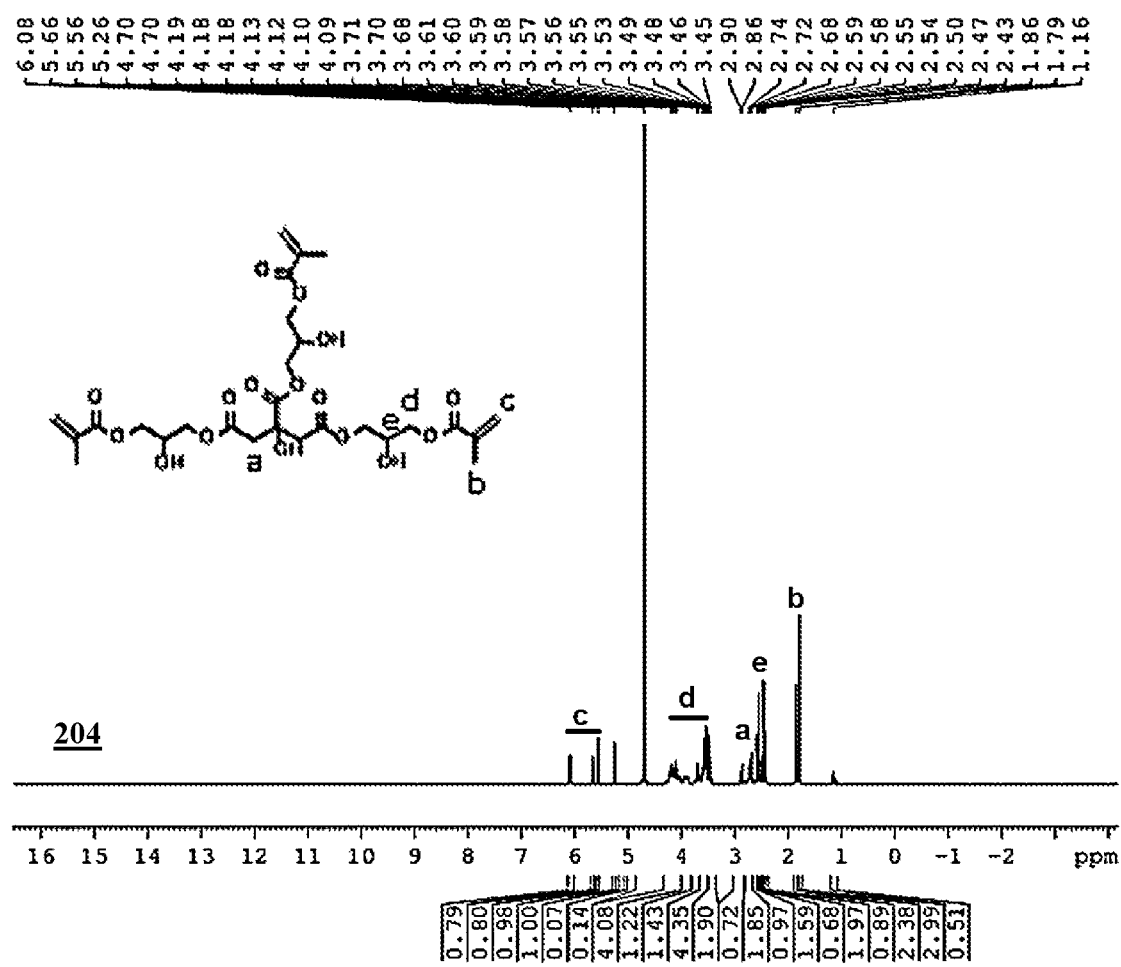
FIG. 2C illustrates a $^1$H NMR spectrum of a citric acid-based crosslinker functionalized using glycidyl methacrylate (CA-GMA), consistent with one or more exemplary embodiments of the present disclosure.

FIG. 2A illustrates a proton nuclear magnetic resonance ($^1$H NMR) spectrum of citric acid (CA) 200, consistent with one or more exemplary embodiments of the present disclosure. FIG. 2B illustrates a $^1$H NMR spectrum of a CA-ECH 202, consistent with one or more exemplary embodiments of the present disclosure. FIG. 2C illustrates a $^1$H NMR spectrum of a CA-GMA 204, consistent with one or more exemplary embodiments of the present disclosure. Referring to FIG. 2A-2C, the comparison between spectra 200 and 202 shows a reduction in the intensity of acidic hydroxyl peaks ("a" and "b") and addition of two other peaks ("c" and "d") for epoxide groups in spectrum 202 of the CA-ECH crosslinkers. Therefore, the acidic hydroxyl groups of the citric acid were used in a reaction of adding epoxide groups to citric acid to form the CA-ECH crosslinkers. Also, the comparison between spectrum 200 and 204 indicates a reduction in the intensity of acidic hydroxyl peaks ("a" and "b") and addition of three other peaks ("c", "d", and "e") for acrylate groups in spectrum 204 of the CA-GMA. Therefore, acidic hydroxyl groups of the citric acid were used in a reaction of adding acrylate groups to citric acid to form CA-GMA crosslinkers.

Figure 3:
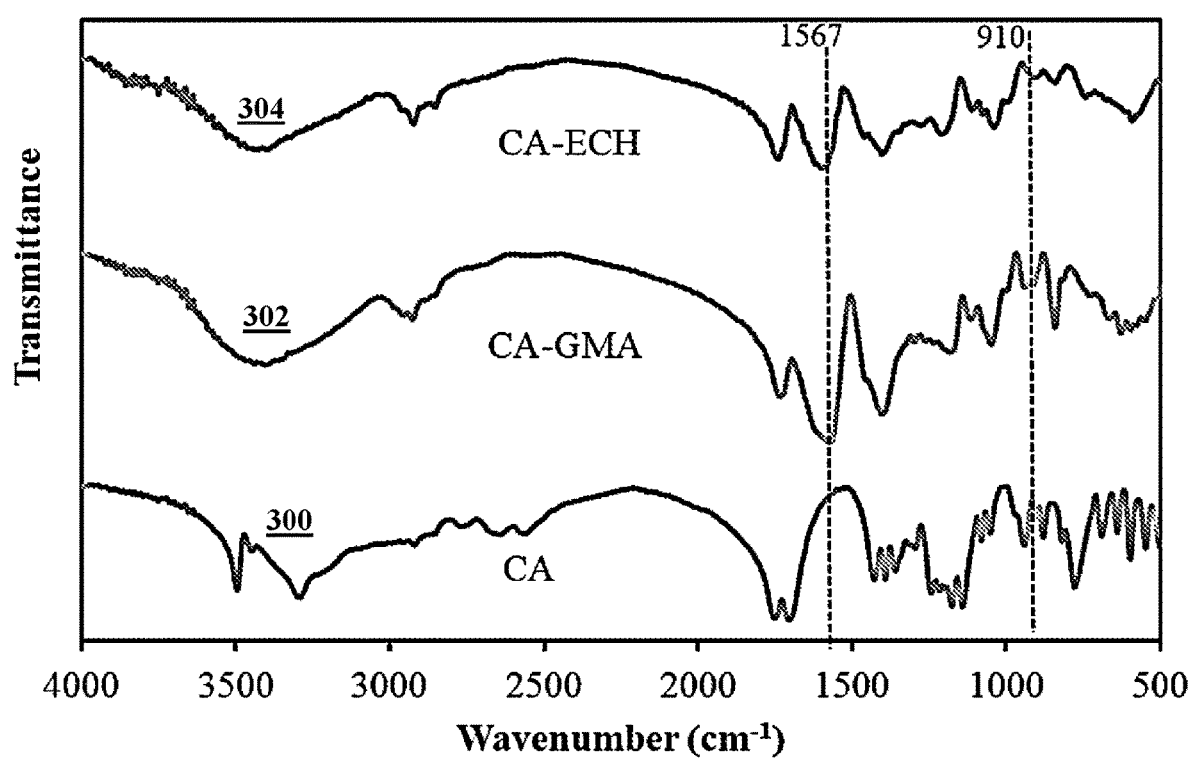
FIG. 3 illustrates Fourier-transform infrared spectroscopy (FTIR) spectra of CA, the CA-ECH, and the CA-GMA, consistent with one or more exemplary embodiments of the present disclosure.

FIG. 3 illustrates Fourier-transform infrared spectroscopy (FTIR) spectra of CA 300, a CA-ECH 302, and a CA-GMA 304, consistent with one or more exemplary embodiments of the present disclosure. Referring to FIG. 3, spectrum 302 of CA-ECH exhibits a peak at a wavelength of 910 cm$^{-1}$ which attributes to epoxy groups and indicates the epoxidation of the CA. Also, spectrum 304 of CA-GMA exhibits a peak at a wavelength of 1567 cm$^{-1}$ which attributes to C=C bonds and indicates the functionalization of CA with GMA.

Figure 4:
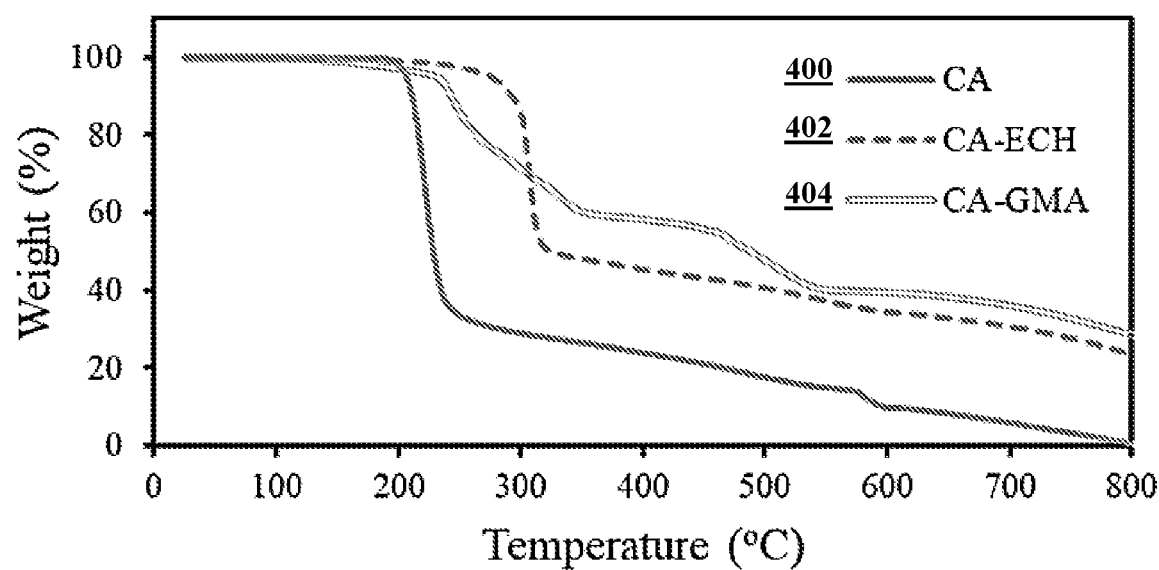
FIG. 4 illustrates thermograms of thermogravimetric analysis (TGA) of CA, the CA-ECH, and the CA-GMA, consistent with one or more exemplary embodiments of the present disclosure.

FIG. 4 illustrates thermograms of thermogravimetric analysis (TGA) of CA 400, a CA-ECH 402, and a CA-GMA 404, consistent with one or more exemplary embodiments of the present disclosure. Referring to FIG. 4, thermogram 402 of CA-ECH and thermogram 404 of CA-GMA show that the steep slopes of the initial weight loss and maximum weight loss were shifted to relatively higher temperatures in comparison with thermogram 400 of citric acid. Also, thermogram 400 shows almost zero residual carbon content which means the complete destruction of citric acid. However, thermogram 402 of the CA-ECH and thermogram 404 of CA-GMA display higher residual carbon content than thermogram 400. Therefore, the thermal stability of CA-ECH and CA-GMA are higher than the thermal stability of citric acid.

Example 2: Synthesis of Functionalized Itaconic Acid-Based Crosslinkers

In this example, functionalized itaconic acid (IA)-based synthesized using GMA and ECH utilizing a process similar to exemplary method 100 as presented in FIG. 1. In order to functionalize the itaconic acid with the GMA, a first mixture was formed by mixing an itaconic acid solution with a NaOH solution. The itaconic acid solution was prepared by dissolving about two (2) grams of itaconic acid in twenty (20) ml of water. Mixing the itaconic acid solution with the NaOH solution was done in a two-necked flask equipped with a magnetic stirrer.

After that, the second mixture was formed by adding the GMA to the first mixture under a stirring condition at a temperature of about 70° C. and for a time period of about two (2) hours. In the next step, the second mixture was washed using toluene at room temperature while stirring and an aqueous phase containing functionalized citric acid was separated. In the end, the functionalized itaconic acid was obtained by drying the aqueous phase at a temperature of about 50° C. in an oven. In the present disclosure, "IA-GMA-1" may refer to itaconic acid-based crosslinkers functionalized using the GMA with a GMA/IA ratio of about two (2) and "IA-GMA-2" may refer to itaconic acid-based crosslinkers functionalized using the GMA with a GMA/IA of about four (4).

Also, in order to functionalize the itaconic acid using ECH, a first mixture was formed by mixing an IA solution with a NaOH solution at a molar ratio of the NaOH/itaconic acid of about 2. After that, a second mixture was formed by mixing the first mixture with a solution of the ECH with a concentration of about 1.75 M in a two-necked flask equipped with a magnetic stirrer. The second mixture contained IA and the ECH with a molar ratio of ECH/IT of about two (2). The second mixture was stirred at a temperature of about 90° C. for a time period of about three (3) hours. In the next step, the second mixture was washed using toluene while stirring and, as a result, an aqueous phase containing functionalized itaconic acid was separated from the second mixture. In the end, the itaconic acid functionalized using the ECH (IA-ECH) was obtained by drying the aqueous phase at a temperature of about 50° C. in an oven.

Example 3: Characterization of Functionalized Tartaric Acid-Based Crosslinkers

In this example, physicochemical characteristics were analyzed of an exemplary functionalized tartaric acid (TTA)-based crosslinker functionalized utilizing a process similar to exemplary method 100 as presented in FIG. 1 using GMA and ECH.

Figure 5A:
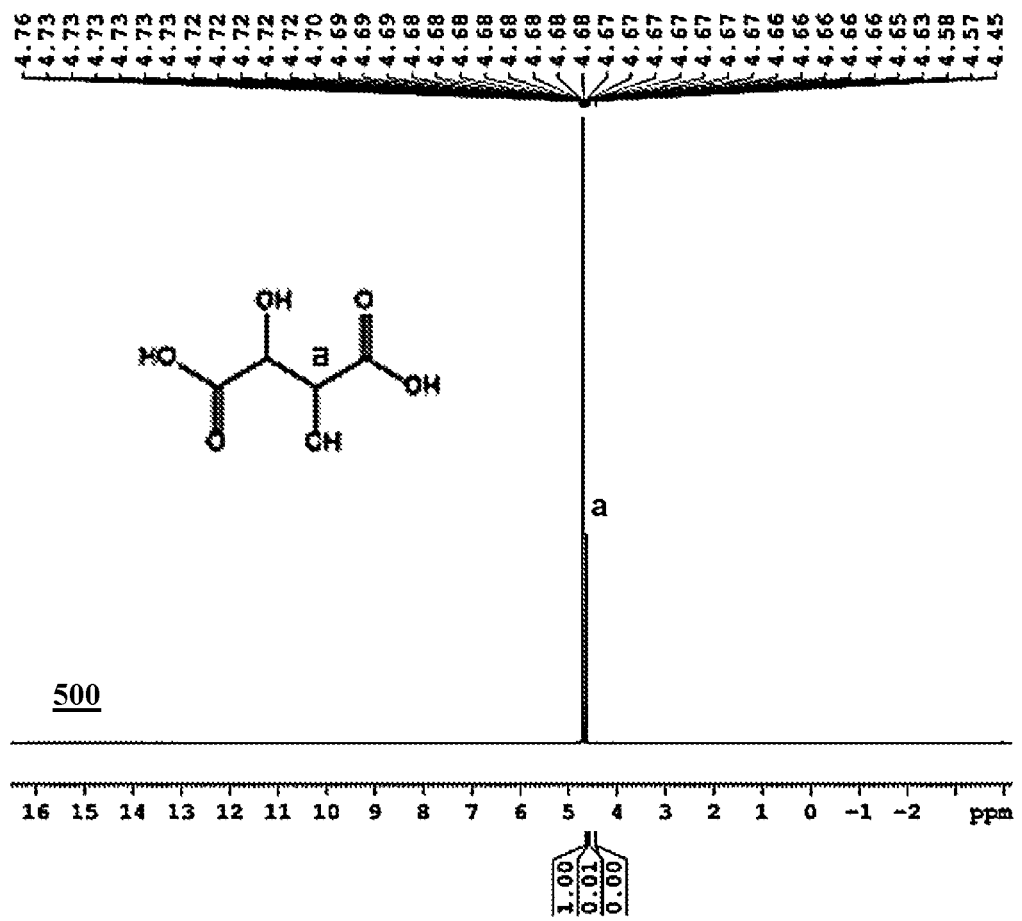
FIG. 5A illustrates a $^1$H NMR spectrum of tartaric acid (TTA), consistent with one or more exemplary embodiments of the present disclosure.
Figure 5B:
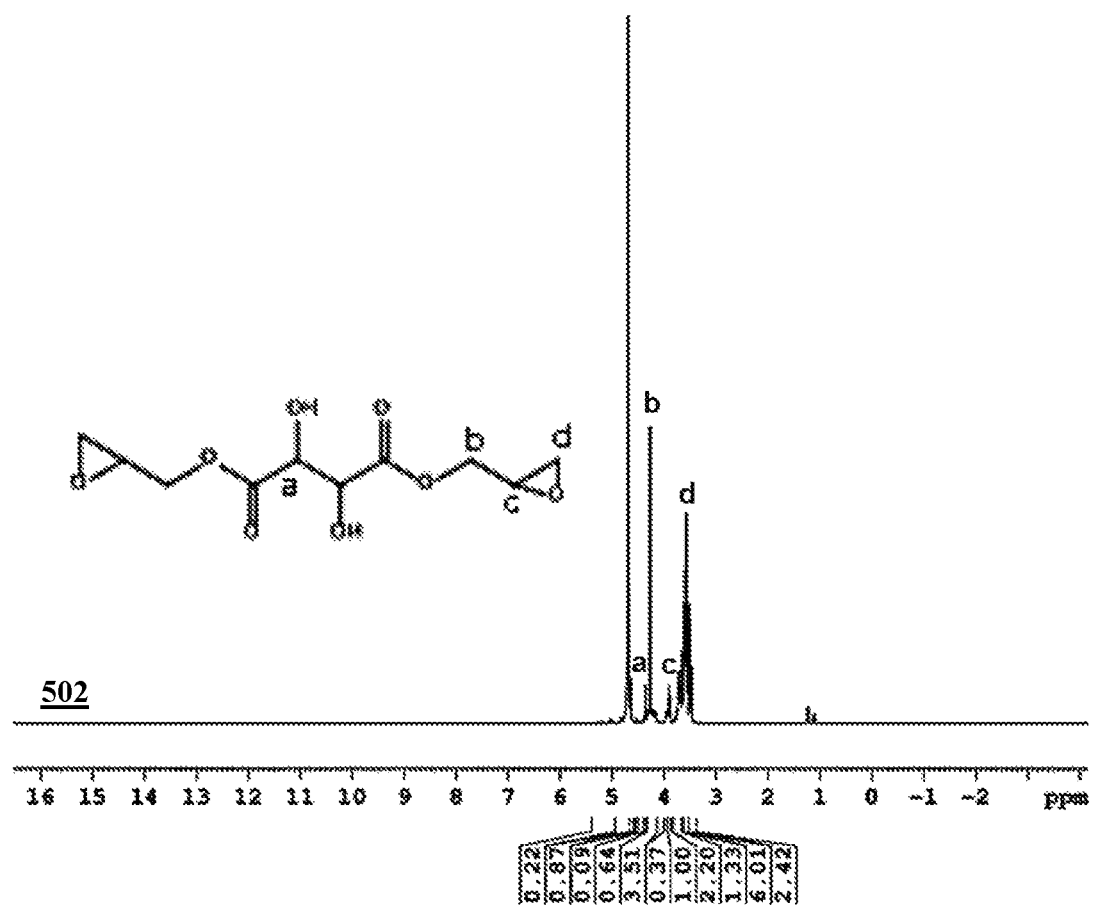
FIG. 5B illustrates a $^1$H NMR spectrum of a tartaric acid-based crosslinker functionalized using epichlorohydrin (TTA-ECH), consistent with one or more exemplary embodiments of the present disclosure.

FIG. 5A illustrates a $^1$H NMR spectrum 500 of TTA, consistent with one or more exemplary embodiments of the present disclosure. FIG. 5B illustrates a $^1$H NMR spectrum 502 of a tartaric acid-based crosslinker functionalized using epichlorohydrin (TTA-ECH), consistent with one or more exemplary embodiments of the present disclosure. Referring to FIGS. 5A and 5B, comparison between spectrum 500 and 502 shows a reduction in the intensity of acidic hydroxyl peaks ("a" and "b") and addition of two other peaks ("c" and "d") for epoxide groups in spectrum 502 of TTA-ECH. Therefore, the acidic hydroxyl groups of the tartaric acid were used in a reaction of adding epoxide groups to tartaric acid to form the TTA-ECH crosslinkers.

Figure 6:
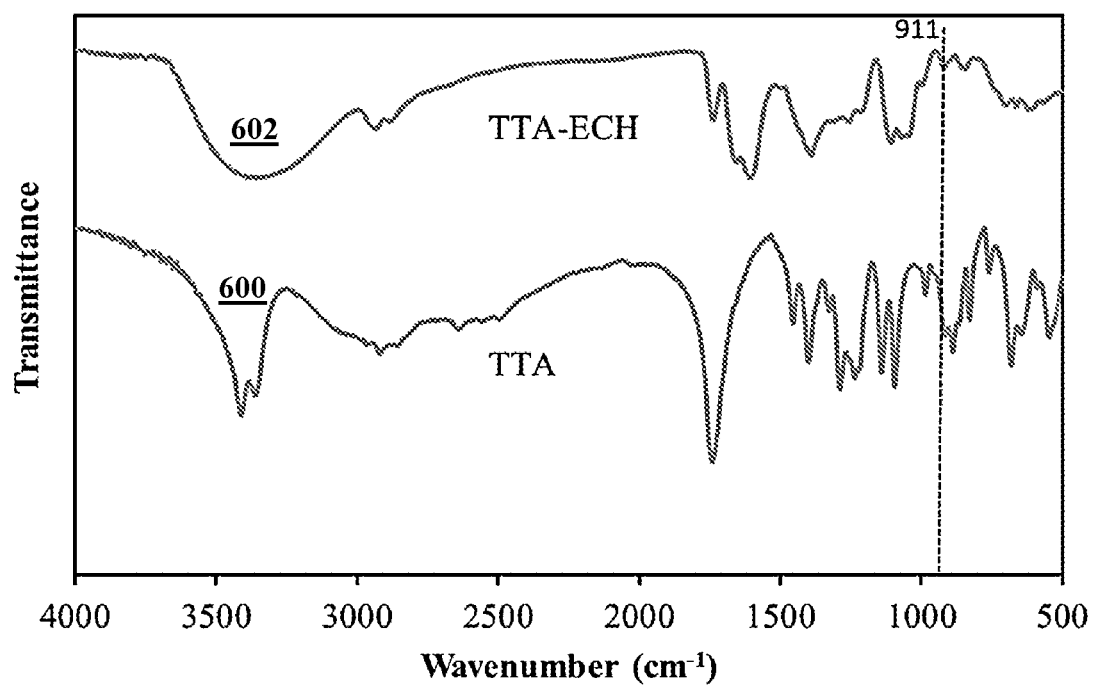
FIG. 6 illustrates FTIR spectra of TTA and the TTA-ECH, consistent with one or more exemplary embodiments of the present disclosure.

FIG. 6 illustrates the FTIR spectra of TTA 600 and TTA-ECH 602, consistent with one or more exemplary embodiments of the present disclosure. Referring to FIG. 6, spectrum 602 of TTA-ECH exhibits a peak at a wavelength of 911 cm$^{-1}$ which attributes to an epoxy group and indicates the epoxidation of TTA.

Figure 7:
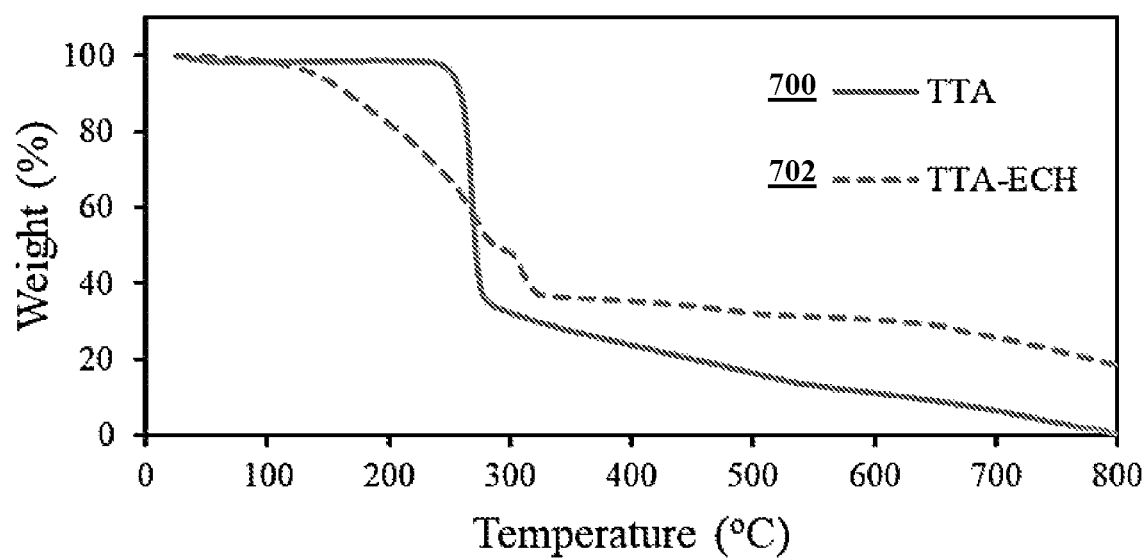
FIG. 7 illustrates TGA thermograms of TTA and the TTA-ECH, consistent with one or more exemplary embodiments of the present disclosure.

FIG. 7 illustrates TGA thermograms of TTA 700 and TTA-ECH 702, consistent with one or more exemplary embodiments of the present disclosure. Referring to FIG. 7, thermogram 702 of TTA-ECH shows that steep slopes of the initial weight loss and the maximum weight loss were shifted to relatively higher temperatures in comparison with thermogram 700 of TTA. Also, thermogram 700 shows almost zero residual carbon content which means the complete destruction of tartaric acid. However, thermogram 702 of TTA-ECH displays higher residual carbon content than thermogram 700. Therefore, the thermal stability of the TTA-ECH is higher than the thermal stability of TTA.

Example 4: Synthesis of Functionalized Succinic Acid-Based Crosslinkers

Figure 8A:
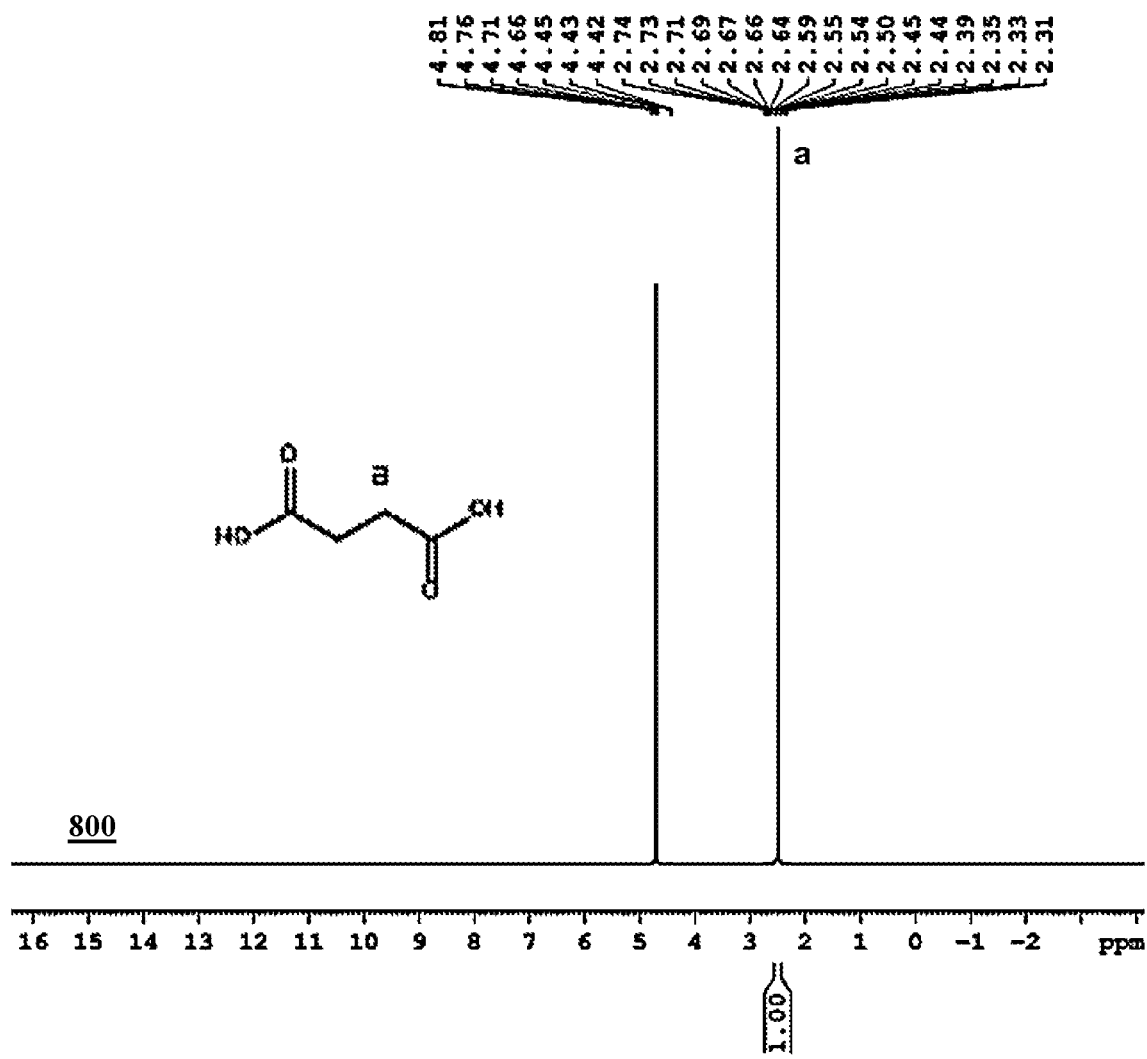
FIG. 8A illustrates a $^1$H NMR spectrum of succinic acid (SA), consistent with one or more exemplary embodiments of the present disclosure.
Figure 8B:
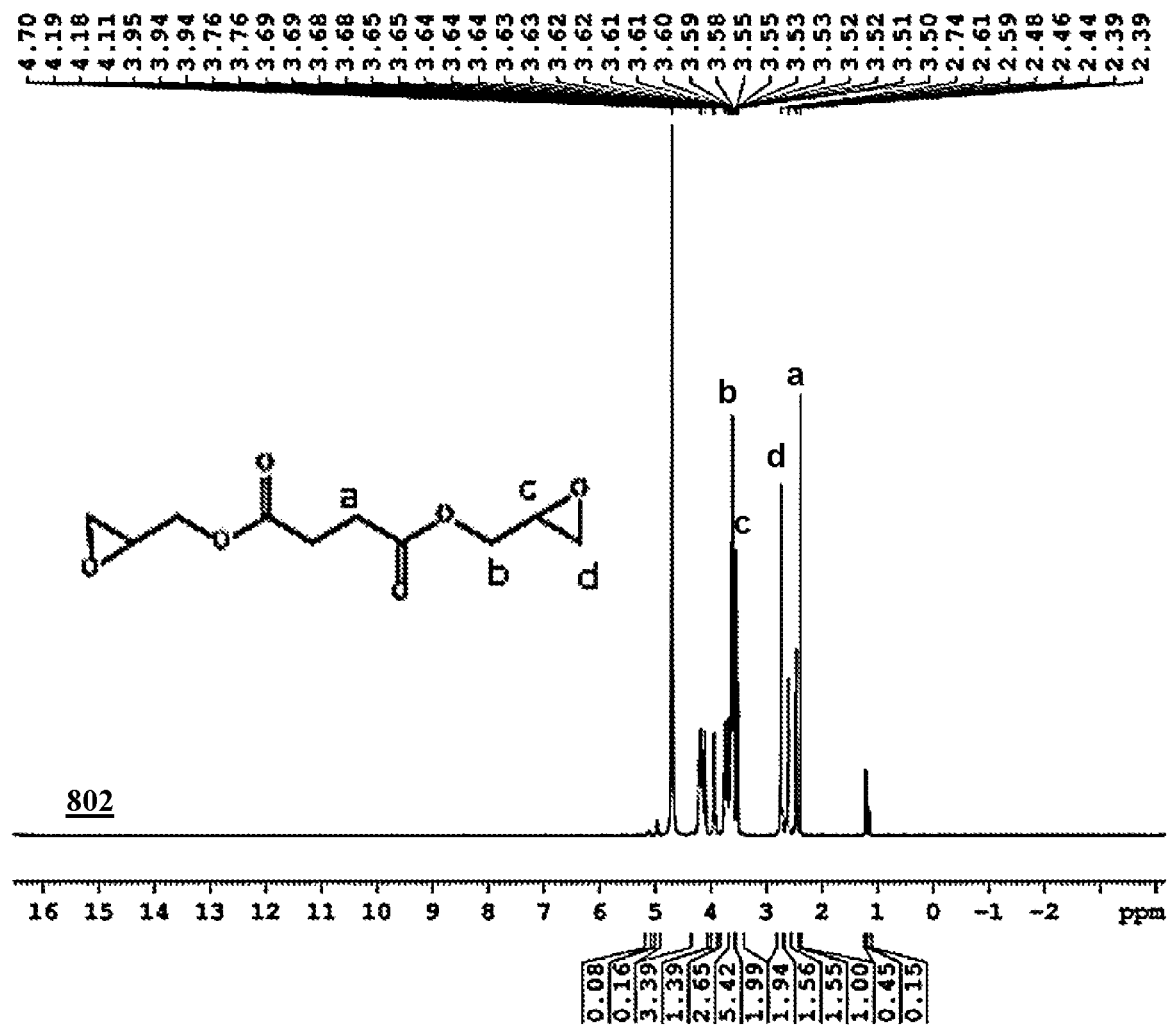
FIG. 8B illustrates a $^1$H NMR spectrum of a succinic acid-based crosslinker functionalized using epichlorohydrin (SA-ECH), consistent with one or more exemplary embodiments of the present disclosure.

In this example, physicochemical characteristics of an exemplary functionalized succinic acid (SA)-based crosslinker functionalized utilizing a process similar to exemplary method 100 as presented in FIG. 1 using GMA and ECH, were analyzed. FIG. 8A illustrates a $^1$H NMR spectrum 800 of SA, consistent with one or more exemplary embodiments of the present disclosure. FIG. 8B illustrates a $^1$H NMR spectrum 802 of a succinic acid-based crosslinker functionalized using epichlorohydrin (SA-ECH), consistent with one or more exemplary embodiments of the present disclosure. Referring to FIGS. 8A and 8B, comparison between spectrum 800 and 802 indicates a significant reduction in the intensity of acidic hydroxyl peaks ("a" and "b") and addition of two other peaks ("c" and "d") for epoxide groups in spectrum 802 of SA-ECH. Therefore, the acidic hydroxyl groups of the succinic acid were used in a reaction of adding epoxide groups to succinic acid to form the SA-ECH crosslinkers.

Figure 9:
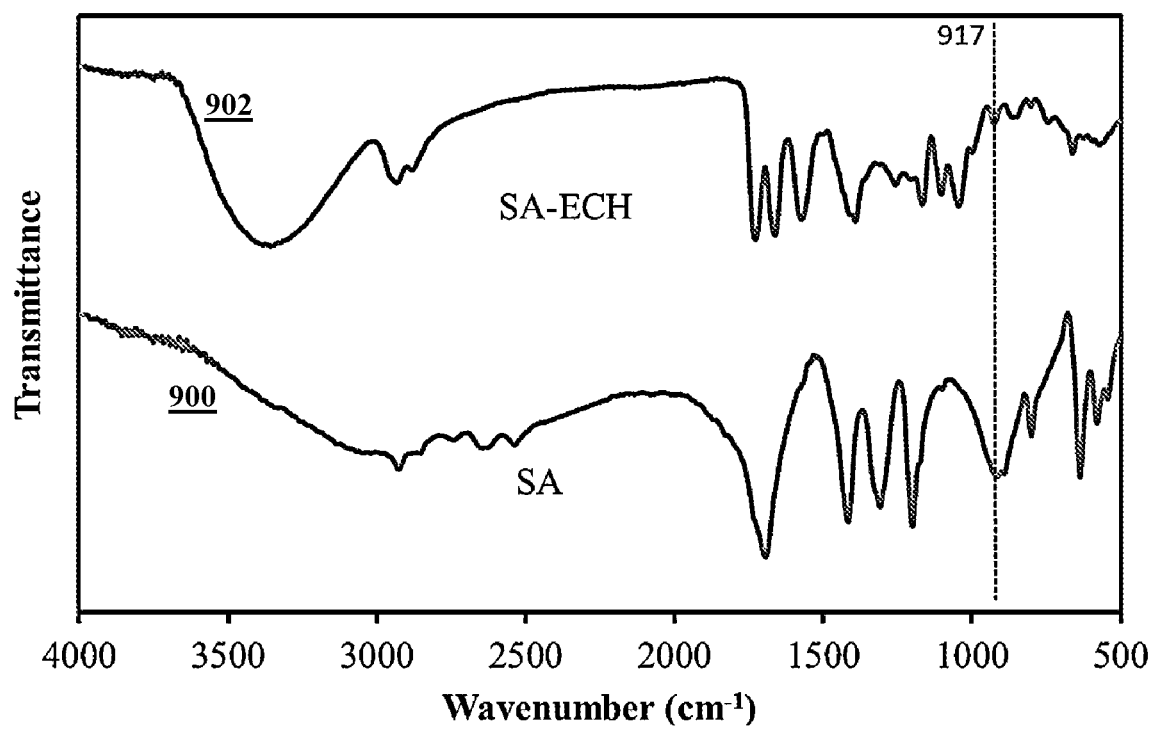
FIG. 9 illustrates FTIR spectra of SA and the SA-ECH, consistent with one or more exemplary embodiments of the present disclosure.

FIG. 9 illustrates the FTIR spectra of SA 900 and SA-ECH 902, consistent with one or more exemplary embodiments of the present disclosure. Referring to FIG. 9, spectrum 902 of the SA-ECH exhibits a peak at a wavelength of 917 cm$^{-1}$ which attributes to epoxy groups and indicates the epoxidation of the SA.

Figure 10:
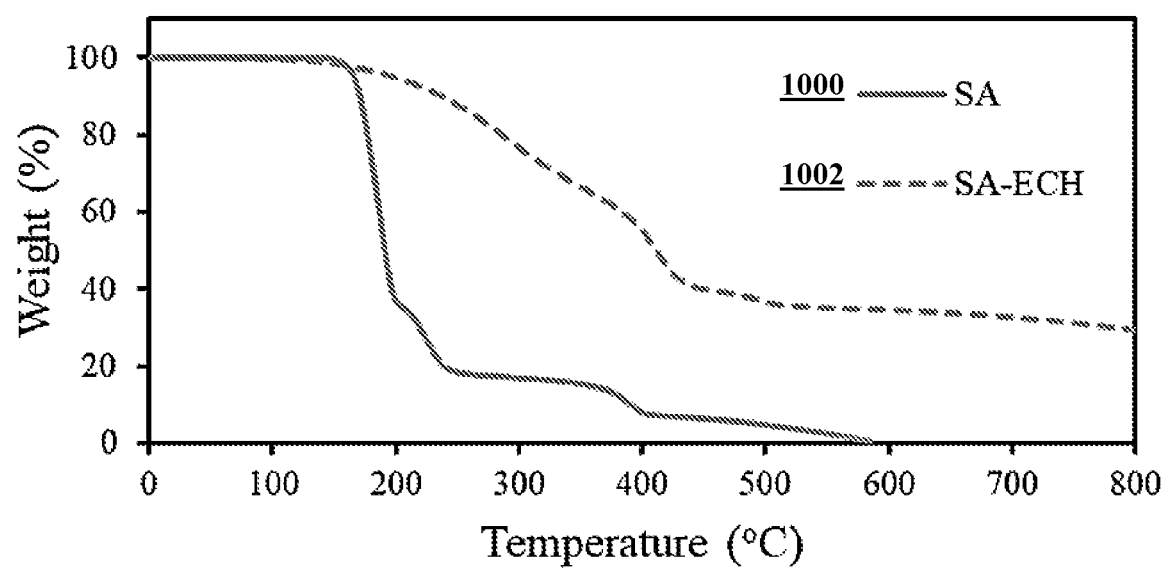
FIG. 10 illustrates TGA thermograms of SA and the SA-ECH, consistent with one or more exemplary embodiments of the present disclosure.

FIG. 10 illustrates TGA thermograms of SA 1000 and SA-ECH 1002, consistent with one or more exemplary embodiments of the present disclosure. Referring to FIG. 10, thermogram 1002 of the SA-ECH shows that the steep slopes of the initial weight loss and maximum weight loss were shifted to relatively higher temperatures in comparison with thermogram 1000 of the succinic acid. Also, thermogram 1000 shows almost zero residual carbon content which means the complete destruction of succinic acid. However, thermogram 1002 of SA-ECH displays higher residual carbon content than thermogram 1000. Therefore, the thermal stability of SA-ECH is higher than the thermal stability of succinic acid.

Example 5: Fabrication and Characterization of Superabsorbent Polymers Containing the Functionalized Bio-Based Crosslinkers In this example, the functionalized bio-based crosslinkers synthesized in EXAMPLE 1 and EXAMPLE 2 were used as an internal crosslinker for fabricating superabsorbent polymers. SAPs were acrylate-based superabsorbent polymers and were prepared via solution polymerization using redox initiation. At first, a mixture was formed by neutralizing acrylic acid with an amount of about fifteen (15) grams using a sodium hydroxide (NaOH) solution at a temperature of about 0° C. The NaOH solution with a concentration of about 5.5 M was prepared by dissolving NaOH into deionized water.

After that, the functionalized bio-based crosslinkers as the internal crosslinker and redox pair initiators were added to the mixture under continuous stirring. The redox pair initiators were ammonium persulfate (APS) and tetraethylmethylendiamine (TEMDA). The reaction time for synthesis of the SAPs was between about 2 minutes and about 30 minutes. In the end, an elastic gel was obtained which is cut and dried to obtain SAP powder. The variable parameter in SAP synthesis is the type and content of the functionalized bio-based crosslinker. The SAPs synthesized using the functionalized bio-based crosslinker require the functionalized bio-based crosslinker with an amount between about 2.5 grams and 10 grams of the functionalized bio-based crosslinker per one (1) Kg acrylic acid.

In the next step, the swelling properties of the exemplary superabsorbent polymers (SAPs) fabricated using the functionalized bio-based crosslinkers were analyzed. The examined properties were swelling capacity in water (Qw), swelling capacity in a saline solution (Qs), and absorbency under load (AUL). TABLE. 2 represents the swelling properties of SAPs fabricated using different types and amounts of IA-GMA as the internal crosslinker. TABLE. 3 represents the swelling properties of SAPs fabricated using different amounts of the IA-ECH in different drying temperatures. Qw refers to swelling capacity in water and Qs refers to saline absorbency. The drying time of the SAPs was about 2 hours.

TABLE 2

Swelling properties of SAPs containing different types of IA-GMA

| Name | Amount crosslinker (g) | Swelling capacity in distilled water (g/g) | Swelling capacity in Saline solution (g/g) | AUL 0.3 psi (g/g) |
| --- | --- | --- | --- | --- |
| IA-GMA-1 | 0.025 | 390 | 61.2 | 7.8 |
| IA-GMA-1 | 0.05 | 362 | 60.4 | 18.8 |
| IA-GMA-1 | 0.2 | 352 | 66.8 | 18.4 |
| IA-GMA-1 | 0.4 | 266 | 64.3 | 19.6 |
| IA-GMA-1 | 0.6 | 278 | 68.1 | 18.6 |
| IA-GMA-1 | 0.8 | 282 | 55.3 | 18.5 |
| IA-GMA-1 | 1 | 254 | 48 | 19.6 |
| IA-GMA-2 | 0.05 | 320 | 65 | 20.5 |
| IA-GMA-2 | 0.1 | 345 | 70.5 | 22.3 |
| IA-GMA-2 | 0.3 | 311 | 72 | 22.5 |
| IA-GMA-2 | 0.5 | 277 | 75 | 22.5 |
| IA-GMA-2 | 1 | 220 | 62 | 21.4 |

TABLE 3

Swelling properties of SAPs containing IA-ECH as the internal crosslinker

| IA-ECH content (g) | Drying temperature (° C.) | Qw (g/g) | Qs (g/g) | AUL (g/g) |
| --- | --- | --- | --- | --- |
| 0.05 | 120 | 1050 | 119 | 13 |
| 0.05 | 140 | 596 | 99 | 15.4 |
| 0.05 | 150 | 412 | 77.2 | 15.9 |
| 0.1 | 120 | 933 | 87.7 | 15.8 |
| 0.1 | 140 | 574 | 79.6 | 16.5 |
| 0.1 | 150 | 397 | 78.3 | 16.6 |
| 0.2 | 120 | 1104 | 116 | 12.7 |
| 0.2 | 140 | 647 | 101 | 15.6 |
| 0.2 | 150 | 339 | 89.5 | 16.6 |

TABLE. 4 represents the swelling properties of SAPs fabricated using different types and amounts of CA-GMA. Also, TABLE. 5 represents the swelling properties of SAPs fabricated using different amounts of CA-ECH. The drying time of the SAPs was about 2 hours.

TABLE 4

Swelling properties of SAPs containing different types of CA-GMA as the internal crosslinker

| Name | Amount of crosslinker (g) | Swelling capacity in distilled water (g/g) | Swelling capacity in a saline solution (g/g) | AUL 0.3 psi (g/g) |
| --- | --- | --- | --- | --- |
| CA-GMA-1 | 0.2 | 196.12 | 52.07 | 18.2 |
| CA-GMA-2 | 0.1 | 221.9 | 60.62 | 12.31 |
| CA-GMA-3 | 0.1 | 269.37 | 54.48 | 13.68 |
| CA-GMA-4 | 0.1 | 233.42 | 53.93 | 17.55 |
| CA-GMA-4 | 0.2 | 198.02 | 60.27 | 18.62 |

TABLE 5

Swelling properties of SAPs containing the CA-ECH as the internal crosslinker

| CA-ECH content (g) | Drying temperature (° C.) | Qw (g/g) | Qs (g/g) | AUL (g/g) |
| --- | --- | --- | --- | --- |
| 0.2 | 140 | 171.28 | 47.64 | 15.85 |
| 0.1 | 120 | 481.20 | 76.65 | 15.66 |
| 0.1 | 140 | 373.55 | 60.79 | 14.98 |

TABLE 5-continued

Swelling properties of SAPs containing the CA-ECH as the internal crosslinker

| CA-ECH content (g) | Drying temperature (° C.) | Qw (g/g) | Qs (g/g) | AUL (g/g) |
|---|---|---|---|---|
| 0.1 | 150 | 249.91 | 44.11 | 12.31 |
| 0.05 | 120 | 532.8 | 55.48 | 11.8 |

Referring to TABLEs. 2-5, the swelling properties of SAPs crosslinked using functionalized bio-based crosslinkers such as saline absorbency and AUL were improved compared to conventional crosslinkers, which makes the functionalized bio-based crosslinkers suitable candidates for using in hygienic SAPs. According to TABLE. 3, the saline absorbency of IA-ECH was up to 119 g/g which is significantly higher than SAPs which are synthesized using conventional crosslinkers. Saline absorbency of commercial superabsorbent with conventional crosslinkers may be between 60 g/g and 70 g/g. Also, the AUL of SAPs which are crosslinked with functionalized bio-based crosslinkers is higher than the AUL value of the SAPs crosslinked with conventional crosslinkers, which is between 8 g/g and 15 g/g. According to TABLE. 2, the SAPs crosslinked using IA-GMA crosslinkers shows AUL value up to 22.5 which is significantly higher than the AUL value of the SAPs crosslinked with the conventional crosslinkers.

While conventional crosslinkers for SAPs, such as polyethylene glycol diacrylate, trimethylolpropantriacrylate, and methylenebisacrylamide are nonionic, functionalized bio-based crosslinkers according to exemplary approaches have an ionic nature due to them containing sodium, potassium, or lithium in their structure. Therefore, the functionalized bio-based crosslinkers have a dissociation ability to produce mobile cations when the SAP is placed in proper swelling media like a saline solution. Without bound by any theory, the higher saline absorbency and the AUL of the SAPs crosslinked using the functionalized bio-based crosslinkers are related to the ionic structure of their internal crosslinkers.

Example 6: Surface Treatment of Superabsorbent Polymers (SAP) Using the Functionalized Bio-Based Crosslinkers Surface treatment of SAPs with external crosslinkers may improve the swelling properties of the SAPs. In this example, the functionalized bio-based crosslinkers synthesized in EXAMPLE 1 were used as an external crosslinker for surface treatment of SAPs. At first, the functionalized bio-based crosslinkers as the external cross-linker was dissolved in a treatment solution containing acetone and water with a weight ratio of about 90:10 w/w. After that, dried SAP particles with an amount of about 5 grams were soaked in the treatment solution. The soaked SAP particles were initially incubated at room temperature for 30 min and then post-treated at different times periods between 1 hour and 3 hours and temperatures between 120° C. and 150° C.

TABLE. 6 represents the swelling properties of surface-treated SAPs using different amounts of IA-ECH. In this example, dried SAP particles were fabricated using IA-GMA-2 with an amount of about 0.1 grams as an internal crosslinker. Then, the fabricated dried SAP particles were surface treated with the IA-ECH at a temperature of about 150° C. for a time period of about 2 hours.

TABLE 6

Swelling properties of the surface-treated SAPs crosslinked using IA-ECH

| IA-ECH content (g) | Qw (g/g) | Qs (g/g) | AUL (g/g) |
|---|---|---|---|
| Intact SAP | 345 | 70.5 | 22.3 |
| 0.1 | 300 | 65.4 | 23.4 |
| 0.2 | 279 | 76 | 30.7 |
| 0.3 | 253 | 67.5 | 24.6 |

Saline absorbency and AUL of SAPs crosslinked using the functionalized bio-based crosslinkers are higher than conventional SAPs. Referring to TABLE. 6, the AUL value of the SAPs crosslinked with the IA-GMA-2 before surface treatment was about 22.3 g/g which is higher than conventional crosslinkers and may be directly used without surface treatment. Moreover, the surface treatment of the SAP with the AUL value of 22.3 g/g increases the AUL value of the SAP to about 30.7 g/g.

TABLE. 7 represents the swelling properties of surface-treated SAPs using different amounts of CA-ECH. In this example, dried SAP particles were fabricated using CA-ECH with an amount of about 0.1 grams as an internal crosslinker. Then, the fabricated dried SAP particles were surface treated with the CA-ECH at a temperature of about 120° C. for a time period of about 2 hours. Referring to TABLE. 7, the surface treatment of SAP with the AUL value of 15.66 g/g increases the AUL value of the SAP to a value of about 18.69 g/g which is an acceptable high value for hygienic SAPs.

TABLE 7

Swelling properties of the surface crosslinked sample with CA-ECH at the different amount

| CA-ECH content (g) | Qw (g/g) | Qs (g/g) | AUL (g/g) |
|---|---|---|---|
| Intact SAP | 481.20 | 76.65 | 15.66 |
| 1 | 216.69 | 42.17 | 18.69 |

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such away. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A method for synthesizing functionalized bio-based crosslinkers, comprising:
    forming a first mixture by mixing itaconic acid with an alkaline solution;
    forming a second mixture containing a functionalized bio-based crosslinker by reacting the itaconic acid with a modifier with a molar ratio of the modifier to the itaconic acid between 2 and 8, the reacting the itaconic acid with the modifier comprising:
        forming a reaction mixture by mixing the first mixture with the modifier, the modifier comprising epichlorohydrin (ECH);
        exposing the reaction mixture to at least one of heating, ultrasound radiation, and microwave radiation; and
    crosslinking acrylic acid monomers by mixing the acrylic acid monomers with the functionalized bio-based crosslinker,
    wherein the mixing the acrylic acid monomers with the functionalized bio-based crosslinker comprises mixing the acrylic acid monomers with the functionalized bio-based crosslinker with a ratio the functionalized bio-based crosslinker to the acrylic acid monomers between 2.5 gram/Kg and 10 gram/Kg.

2. The method of claim 1, wherein exposing the reaction mixture to at least one of the heating, the ultrasound radiation, and the microwave radiation comprises heating the reaction mixture to a temperature between 30° C. and 95° C.

3. The method of claim 2, wherein heating the reaction mixture comprises heating the second mixture for a time period between 30 minutes and 6 hours.

4. The method of claim 1, wherein mixing the itaconic acid with the alkaline solution comprises mixing the itaconic acid with the alkaline solution at a molar ratio of alkaline material/itaconic acid between 2 and 5.

5. The method of claim 4, wherein mixing the itaconic acid with the alkaline solution comprises mixing the itaconic acid with at least one of sodium hydroxide, lithium hydroxide, and potassium hydroxide.

6. A method for synthesizing functionalized bio-based crosslinkers, comprising:
    forming a first mixture by mixing itaconic acid with an alkaline solution; and
    forming a second mixture containing a functionalized bio-based crosslinker by reacting the itaconic acid with a modifier with a molar ratio of the modifier to the itaconic acid between 2 and 8, the reacting the itaconic acid with the modifier comprising:
        forming a reaction mixture by mixing the first mixture with the modifier, the modifier comprising epichlorohydrin (ECH);
        exposing the reaction mixture to at least one of heating, ultrasound radiation, and microwave radiation; and
    crosslinking acrylic acid monomers by mixing the acrylic acid monomers with the functionalized bio-based crosslinker,
    wherein mixing the acrylic acid monomers with the functionalized bio-based crosslinker further comprises mixing a redox pair initiator with the acrylic acid monomers and the functionalized bio-based crosslinker, the redox pair initiator comprising ammonium persulfate (APS) and tetraethylmethylendiamine (TEMDA).

7. The method of claim 6 further comprising:
    forming a purified mixture containing the functionalized bio-based crosslinker by washing the second mixture with an antisolvent; and
    obtaining the functionalized bio-based crosslinker by drying the purified mixture.

* * * * *